(12) United States Patent
Dirks et al.

(10) Patent No.: US 7,860,658 B2
(45) Date of Patent: Dec. 28, 2010

(54) REVERSE PROGENY MAPPING

(75) Inventors: Robert Helene Ghislain Dirks, Oudenbosch (NL); Johannes Wilhelmus Schut, Wouw (NL)

(73) Assignee: Rijk Zwaan Zaadteelt En Zaadhandel B.V., De Lier (NL)

( * ) Notice: Subject to any disclaimer, the term of this patent is extended or adjusted under 35 U.S.C. 154(b) by 304 days.

(21) Appl. No.: 11/848,800

(22) Filed: Aug. 31, 2007

(65) Prior Publication Data

US 2008/0057583 A1 Mar. 6, 2008

Related U.S. Application Data

(63) Continuation-in-part of application No. PCT/EP2006/002096, filed on Mar. 2, 2006.

(30) Foreign Application Priority Data

Mar. 3, 2005 (EP) ................................. 05075519
Jan. 6, 2006 (EP) ................................. 06075041

(51) Int. Cl.
*G06F 7/00* (2006.01)

(52) U.S. Cl. .............................. 702/19; 702/20; 703/11; 703/13; 707/600; 435/6; 435/41; 435/242; 435/440

(58) Field of Classification Search ........................ None
See application file for complete search history.

(56) References Cited

U.S. PATENT DOCUMENTS

2006/0179498 A1* 8/2006 Dirks et al. .................... 800/14

FOREIGN PATENT DOCUMENTS

| WO | WO 99/32661 | | 7/1999 |
| WO | WO03017753 | * | 1/2003 |
| WO | WO 2005/014858 | | 2/2005 |

OTHER PUBLICATIONS

Chesler et al. Neuroinformatics vol. 1, 2003 p. 343-358.*

F. Bretagnolle, et al., Tansley Review No. 78 Gametes With the Somatic Chromosome Number: Mechanisms Of Their Formation And Role In The Evolution Of Autopolyploid Plants, New Phytol. (1995) vol. 129, p. 1-22.

J. A. Buso, et al., Chromosome Regions Between Centromeres And Proximal Crossovers Are The Physical Sites Of Major Effect Loci For Yield In Potato: Generic Analysis Employing Meiotic Mutants, PNAS (1999) vol. 96, p. 1773-1778.

Christiane Deslauriers, et al., Flow Cytometric Characterization And Sorting Of Cultured *Brassica Napus* Microspores, Biochimica et Biophysics Acta (1991) vol. 1091, p. 165-172.

M.S. Ramanna, et al., Relevance Of Sexual Polyploidization For Crop Improvement—A Review, Euphytica (2003) vol. 133, p. 3-18.

Keiichi Okazaki, et al., Induction Of 2n Pollen In Tulips By Arresting The Meiotic Process With Nitrous Oxide Gas, Euphytica (2005) vol. 143, p. 101-114.

Jaap M. van Tuyl, et al., Identification Of 2n-Pollen Producing Interspecific Hybrids of Lilium Using Flow Cytometry, Cytologia (1989) vol. 54, p. 737-745.

Xin-Zhong Zhang, et al., Creating Triploid Germplasm Via Induced 2n Pollen In *Capsicum Annuum* L., Journal of Horticultural Science & Biotechnology (2002) Vo. 78 No. 1, p. 84-88.

* cited by examiner

*Primary Examiner*—Mary K Zeman
(74) *Attorney, Agent, or Firm*—Vedder Price P.C.; Thomas J. Kowalski; Smitha B. Uthaman

(57) ABSTRACT

Provided is a method for mapping traits in organisms, in particular in plants. The method comprises a) providing a population of SDR-0 organisms, in particular plants, that each arise from one member of a population of unreduced cells resulting from second division restitution, in particular a population of unreduced spores; b) producing SDR-1 progeny populations of each of these SDR-0 organisms; c) phenotyping the SDR-1 progeny populations to identify segregating traits within each SDR-1 progeny population; d) if segregating progeny are present in a SDR-1 progeny population, genotyping the corresponding SDR-0 organism and comparing the genotype thereof with the genotype of the other SDR-0 organisms to identify heterozygous chromosomal regions associated with the occurrence of the segregating trait identified in the SDR-1 progeny population.

17 Claims, 14 Drawing Sheets

Parent A  ×  Parent B

Hybrid AB

Meiosis 1: chromosome doubling

Meiosis 1: recombination took place

● = centromere

Meiosis 2: formation of spores/gametes

Groups of recombined/parental chromosomes 3 possible examples of spores/gametes

Corresponding "Doubled Haploids"

Second division does not take place = second division restitution 4 examples of spores/gametes (SDR-0):
note the partial heterozygocity (1)　　　　　　(2)　　　　　　(3)

(4)

(3)

Meiosis 1: chromosome doubling

Meiosis 1: recombination took place

Possible gametes from 1 recombination event from 1 SDR event

REVERSE PROGENY MAPPING

CROSS-REFERENCE TO RELATED APPLICATIONS

This application is a continuation-in-part of International application no. PCT/EP2006/002096, filed Mar. 2, 2006, published as WO 2006/094774 on Sep. 14, 2006, and claiming priority to EP 05075519.8, filed Mar. 3, 2005 and EP 06075041.1, filed Jan. 6, 2006.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to a method for mapping traits in organisms, in particular in plants.

BACKGROUND OF THE INVENTION

Complex crop traits such as yield, stress tolerance, metabolite composition and related phenomena such as heterosis and combining ability are difficult to study due to their quantitative genetic nature and strong interaction with the environment. In addition, the genetics of such traits/phenomena caused by them is very often also complex and mostly quantitative and polygenic, which means that the resulting phenotype is caused by the interaction of the different alleles that are encoded by different genetic loci.

Attempts to characterise the individual loci that contribute to a quantitative trait have been successful when each of the individual loci has a measurable contribution to the total effect irrespective of the presence or absence of alleles of the other loci, which contribute to the quantitative trait. In this case the individual QTLs as they are called are of an additive nature and inherit in a simple Mendelian fashion.

Several methods for QTL mapping have been extensively described, however most of these methods fail when phenotypes are caused by the interaction of numerous heterozygous loci, especially when such loci are interdependent. This means that two or more specific loci need to be present simultaneously for the expression of a specific trait. In the absence of the required alleles on either of the two loci the phenotypic trait will not be expressed. The individually required alleles can occur either in homozygous or heterozygous form. Depending on the specific trait, different genetic constitutions of the loci may be required. For instance a measurable effect is only observed when 2 or more loci are present in heterozygous state and no effect is observed when either locus is homozygous. In such a case, one could state that such loci are interdependent.

As mentioned before, complex traits such as yield and stress tolerance, are of high industrial importance, and therefore, it is highly desirable to have tools like molecular markers linked to these complex traits, which allow for increased efficiency of breeding for such traits in different crops.

Contemporary plant breeding is routinely using genetic (molecular) marker technologies such as AFLP, RAPD's, SSR's, SNP's etc, for a review see e.g. Lakshmikumaran, T. et al., *Molecular markers in improvement of wheat and Brassica*. In: Plant Breeding—Mendelian to Molecular approaches. H. Jain and M. Kharkwal (eds.) Copyright 2004 Narosa Publishing House, New Delhi, India, page 229-255.

Molecular markers are very desirable as diagnostic tools that indicate the presence of a particular trait even in a developmental stage during which the trait is not expressed. In addition, molecular markers are insensitive to environmental conditions.

As an example, molecular markers (for example in the form of SNP=single nucleotide polymorphism, or associated with DNA bands on agarose or polyacrylamide gels) can be found that are genetically linked to genes that are responsible for the colour of pepper fruits when they are ripe. A DNA sample taken from a seedling can be used to determine which colour the fruits of the plant will eventually have. So in this case there is a direct association between the presence of a particular DNA sequence that is being "called" and the presence of a particular trait.

In essence, the same procedure is true for many polygenic traits (see e.g. Tanksley S., *Mapping polygenes*, Annu. Rev. Genet. 1993, 27: 205-233). In the latter case, the trait, whatever it may be, for instance disease resistance, resistance to stress, production of vitamins etc., may be controlled by more than one locus. It is assumed that the contribution of every individual locus, and its associated DNA marker can be measured and that the sum of the different loci and their respective DNA markers will phenotypically result in the presence of the particular trait (to some extent). This concept traces back to the classical work of R. A. Fisher (*The correlations between relatives on the supposition of Mendelian inheritance*, Trans. R. Soc. Edinb. (1918) 52, 399-433), who linked Mendelian genetics with earlier statistical approaches of correlation between relatives, to explain quantitatively inherited traits.

Eukaryote chromosome mapping by recombination is a well know technique for the person skilled in the art (Griffiths A J F et al., (2005) Eukaryote chromosome mapping by recombination, In: *Introduction to Genetic Analysis*, 8th edition. W. H. Freeman and Company, New York p 115-137).

The mapping of segregating traits, i.e. QTL-mapping (QTL=Quantitative Trait Locus), is not solely dependent on technical issues or recombination but equally important is the accurate observation or scoring, qualitatively or quantitatively, respectively, of the phenotype. In this respect, when mapping complex traits or effects, the person skilled in the art is preferentially using a population of doubled haploid lines (DH) or a population of recombinant inbred lines (RIL), which are segregating for the trait(s) of interest, and which are derived from a single F1 plant.

DH-lines are derived directly from the haploid F1-plant gametes, by plant regeneration and chromosome doubling. RILs are highly inbred lines, derived by single seed descent (SSD), i.e. via inbreeding over several generations, where each individual plant provides one seed for the next generation, starting in the F2.

Alternatively, so called Near Isogenic Lines (NIL) are used. NILs are homozygous lines that differ for a small DNA fragment. They are usually derived from backcrosses, but can also be obtained from segregating RILs (Tuinstra et al., (1997) *Theor. Appl. Genet.* 95: 1005-1011).

DH-lines, RILs and NILs greatly contributed to contemporary genetics and genetic mapping. The advantage of such pure lines exactly lies in the fact that phenotypic variation between lines (inter-line variation) is easily recorded as compared to segregation at the level of individual plants for a classical F2 mapping population. The availability of pure lines is of course increasingly important as also environmental influence may be accounted for by replication of genetically identical plants of a pure line. This in contrast to single, unreplicated, individual F2-plant phenotypes that are the product of the interaction of genes and environment.

The elucidation of complex effects such as heterosis or combining ability between lines is one of the biggest challenges for contemporary genetics and plant breeding. For heterosis, several hypotheses have been formulated (see e.g. Birchler J et al. (2003) *The plant Cell* 15, 2236-2239). The so-called historical explanations for heterosis are "overdominance" and dominance. Overdominance refers to the idea that allelic interactions occur in the hybrid such that the heterozygous class performs better than either homozygous class. Dominance refers to the situation in which the suboptimal recessive allele of one parent is complemented by the dominant allele of the other parent. Whereas heterotic effects explained by dominance can in principle be fixed in a homozygous state, it is obvious that for effects explained by overdominance this is impossible. It has recently become clear that the two competing single-locus explanations for heterosis are insufficient and that also epistatic effects, i.e. inter-locus interactions, play a major role as the genetic basis of heterosis (Yu S B et al. (1997) *Proc. Natl. Acad. Sci. USA* 94: 9226-9231).

As mentioned before, traditionally used mapping population structures with homozygous individuals, such as Recombinant Inbred Line populations (RILs) and Doubled Haploid (DH) populations, cannot easily be applied for mapping the specific effect of the heterozygous state at a certain locus. This disadvantage has been overcome by crossing these populations with testers, and assessing the phenotypes of the offspring hybrids. However, this approach has three disadvantages. First, it requires additional labour, space and time. Furthermore, it compares the heterozygous state of a locus with only one of the two possible homozygous states, unless at least one additional tester is used. And finally, it does not fully assess the interaction between the heterozygous locus and the genetic background, i.e. gene interaction with specific effects due to heterozygosity.

The use of diallel mating populations, as proposed by Charcosset et al. (1994) and Rebaï et al. (1994) (both in: Biometrics in plant breeding: applications of molecular markers; Eds: Ooijen J. and Jansen J. CPRO-DLO, Wageningen, The Netherlands), overcomes part of the latter two disadvantages, but requires even more labour and space.

F2- and back-cross populations can be applied to assess for mapping the specific effect of the heterozygous state at a certain locus. However, only limited gene interaction is allowed in the F2-based QTL-analysis, because of the available parameter space in the statistical model, which is limited by population size. Backcross populations require more time and labour to produce them, and the effect of the heterozygous state at a certain locus is only estimated for the genetic background of the recurrent parent, without taking into account possible interactions with other loci.

Another approach to avoid large investments in time, space and labour to develop mapping populations is linkage disequilibrium mapping (LD-mapping; Kraakman A T W et al. (2004) *Genetics* 168, 435-446; Kraft T et al. (2000) *Theor. Appl. Genet.* 101, 323-326). This method makes use of available existing genetic material, such as varieties and genebank accessions. If this material is sufficiently heterozygous, for example a mapping set of hybrid varieties, it is possible to estimate the specific effect of the heterozygote loci. However, in general LD-mapping methods do not consider epistatic effects and require large numbers of accessions to detect additively working QTLs within the statistical noise caused by the epistatic effects, which are due to the different genetic backgrounds across all accessions. (Flint-Garcia S A et al. (2003) *Annu. Rev. Plant Biol.* 54, 357-374).

Traits that are dependent on the combination of the allelic constitution of two or more loci are much more difficult to identify or map. In population genetics this interaction between several loci is called 'epistasis'. In this case the contribution of one locus is only measurable in a certain allelic constitution of another or a third or fourth etc. locus.

In a simple theoretical case one could imagine that a homodimeric enzyme that is encoded by a specific gene (1 locus) may be more effective in catalysis if the dimers are slightly different (1 locus but 2 alleles in the heterozygote) so that, for instance, a more effective catalytic site is formed. In this case AA' is superior in catalysis as compared to AA or A'A'. In addition to that, it is well possible that in a biosynthetic pathway this enzyme encoded by the "A" gene (whatever the genetic composition may be) could be dependent on the catalysis of another enzyme that is upstream or downstream of the particular enzyme in the cascade. It can be easily understood that if the enzyme "A" becomes more efficient, that this increase in efficiency can only be effectively executed if there is no limitation in the substrate that "feeds" the "A" encoded enzyme. In the case the substrate used by the A enzyme is provided by another enzyme (B) whereby the same rule is true (homodimeric enzyme improved by 2 alleles) then improvement is only obtained by the combination. In that case AA'/BB' is better than AA/BB' or AA'/BB and all the other combination where both heterozygous states would be absent.

If, on the other hand, the output of the pathway is not limited anymore by the step that A is controlling, but if an enzyme downstream of A constitutes the limiting step, than the effect of different alleles of A is not measurable and so the locus that is responsible for the enzyme downstream of A is epistatic to A.

A well know example where heterozygote individuals are superior versus homozygous individuals is sickle-cell anemia. Investigation into the persistence of an allele that is so obviously deleterious in homozygous individuals led to the finding that the allele confers a small but significant resistance to lethal forms of malaria in heterozygous individuals. Natural selection has resulted in an allele population that balances the deleterious effects of the homozygous condition against the resistance to malaria afforded by the heterozygous condition.

It is obvious that superior heterozygosity and epistasis may be present simultaneously and the effects described for homodimers can also be valid for heteromultimers.

In conclusion, this means that the contribution of one particular locus on its own cannot easily be measured or visualized, because at least part of the contribution of the individual locus is non-additive and interacting with the allelic state of one or more other loci. Therefore QTL mapping of epistatic traits cannot easily be done by traditional methods, which are generally assuming additivity between loci. Incorporation of inter-locus-interactions in these methods often results in problems with statistical parameter estimation and low power to detect QTLs, due to the high parametrisation of the genetic models used for this purpose.

Alternative methods trying to solve this problem, are QTL x genetic background mapping, which is applied on diallel mating populations (Charcosset A et al. (1994) pp 75-84 and Rebaï A et al. (1994) pp 170-177, both in: *Biometrics in plant breeding: applications of molecular markers*; Eds: Ooijen J and Jansen J. CPRO-DLO, Wageningen, The Netherlands), and QTL x population-mapping, applied on multiple related inbred-line crosses (Jannink J-L & Jansen R (2001) *Genetics* 157: 445-454). The latter state that such methods can also be applied to other populations structures.

An interesting population structure for the purpose of detection of epistatic interactions is the Heterogeneous Inbred Family (HIF) (Haley S et al., (1994) *Theor. Appl. Genet.* 88, 337-342; Tuinstra M et al., (1997) *Theor. Appl. Genet.* 95: 1005-1011), because of its 'multiple ceteris paribus' property, i.e. the family contains many possible subpopulations, where in each of them only one QTL is segregating in a specific homozygous background for the other QTLs.

The construction of HIF-populations is very tedious. It takes several generations of single seed descent, which means it is slow and labour-demanding. By the time the HIF-population is completed the chosen population parents may not be up to date anymore. Facilities or alternative locations to decrease generation time require high investments. Also considering the fact that QTL-alleles of only two parents are analysed, it is often not worth to invest in such populations for commercial breeding purposes.

A more pragmatic approach for QTL-mapping in the presence of epistasis is presented in U.S. Application No. 2005/0015827. The position and effect of QTLs in the background given as it is in the ongoing breeding program is recurrently monitored. No specific population structure is applied, as in linkage disequilibrium mapping (see below), and changes in position and effect of QTLs are accepted as a fact of life. The main disadvantages of this method are the high number of accessions that have to be analysed and the lack of analytical power to establish specific epistatic effects. In other words, it is not analysed which specific locus in the genetic background is interacting with the changing QTLs.

A more radical way of avoiding epistatic effects in QTL-analysis is the use of backcross populations. In this way QTL-effects can be analysed in a more or less constant genetic background, namely that of the recurrent parent. Most backcross population types (for instance backcross inbred lines or BIL's) can be seen as analogues of regular mapping population types where one or more backcrossing generations have been included to create a more uniform genetic background, and in several cases, rule out one of the three allelic states of a locus.

In view of the above it is the object of the present invention to provide a method for mapping traits in organisms, in particular plants, that does not have the above described drawbacks.

SUMMARY OF THE INVENTION

The present invention is based on the finding that it is possible to readily map the loci that encode complex traits by making use of gametes, derived from a particular class of abnormal meiotic divisions, and phenotyping the progeny of organisms regenerated from such gametes.

The method of the invention, which is called herein "Reverse Progeny Mapping" or "RPM", is based on the use of cells, in particular spores, that are formed due to an abnormality in the second division of meiosis, so called Second Division Restitution or SDR and by consequence these spores are diploid (when the parental plant was also diploid) in contrast to normal spores that are haploid. Such spores are called SDR-0 spores and the plants regenerated therefrom are SDR-0 plants.

Second division restitution is just one case of a broader class of said unreduced spores/gametes. Veilleux R, ((1985) *Plant Breeding Reviews* 3, 253-288), describes the mechanisms by which unreduced gametes are formed and provides a list of the occurrence of unreduced gametes in crop plants. At that time mainly 2 different classes of unreduced gametes were recognized namely Second Division Restitution (SDR) and First Division Restitution (FDR). Recently, a third class of unreduced gametes has been published named Indeterminate Meiotic Restitution (IMR) (Lim K et al. (2001) *Theor. Appl. Genet.* 103:219-230). For the purpose of this invention only SDR is relevant. Another publication that shows that SDR is a natural and widespread phenomenon is Lim K et al. (2004) *Breeding Science* 54:13-18.

Due to crossing-over during meiosis I the chromosomes of SDR-0 spores may have segments that are heterozygous. In the context of the present invention heterozygocity means that the alleles of a gene of the hybrid starting plant are polymorphic, whereas homozygosity means that the alleles of a gene are identical.

When spores produced through SDR are regenerated, diploid plants are obtained with on average a reduced level of heterozygosity as compared to plants obtained through normal meiosis and selfing (F2 generation). It is estimated that on average SDR events contain 60% homozygocity (starting from a 100% heterozygous hybrid plants) whereas this is 20% for FDR events. The actual level depends on the number and relative position to the centromere and of the crossing-overs, which have occurred during the specific SDR event.

Only loci that are located on the heterozygous segments in SDR-0 plants can segregate. Segregation takes place in the next generation, named SDR-1. The genotype that will produce a specific phenotype in the SDR-1 generation will be different from the genotype in the SDR-0 generation. However, segregating phenotypes in the SDR-1 generation can only occur if the SDR-0 plant was to some extent heterozygous. This means that it is sufficient to determine in the SDR-0 generation which loci are heterozygous in order to position the loci that are responsible for the segregating phenotype in the SDR-1 generation. Identification and localisation of the crossing-over breakpoints in the individual SDR-0 plants predicts and by consequence maps the position of the locus that is responsible for the segregation of a particular phenotypic trait in the SDR-1 progeny.

The present invention thus relates to a method for mapping traits in organisms, in particular in plants, comprising the steps of:

a) providing a population of SDR-0 organisms, in particular plants, that each arise from one member of a population of unreduced cells resulting from second division restitution, in particular a population of unreduced spores;

b) producing SDR-1 progeny populations of each of these SDR-0 organisms;

c) phenotyping the SDR-1 progeny populations to identify segregating traits within each SDR-1 progeny population;

d) if segregating progeny is present in a SDR-1 progeny population genotyping the corresponding SDR-0 organism and comparing the genotype thereof with the genotype of the other SDR-0 organisms to identify heterozygous chromosomal regions associated with the occurrence of the segregating trait identified in the said SDR-1 progeny population.

In a specific embodiment, the population of unreduced cells that each give rise to a plant of the SDR-0 population is obtained by sorting a population of cells, in particular spores, on the basis of size, mass or DNA content and selecting the cells, in particular spores, that have an increased size, mass or DNA content as members of the population of unreduced cells, in particular unreduced spores. The cells, in particular spores, may be sorted by means of a flow cytometer, centrifuge, manually with a micromanipulator or by any other sorting means.

Phenotyping the SDR-1 progeny populations can be performed in any way known to the person skilled in the art and can in particular be done by means of visual observation or by analysis of the content and/or composition of ions, transcripts, proteins, metabolites, or combinations thereof in each SDR-1 organism. Analysing the content and/or composition of ions, transcripts, proteins, metabolites is for example done with technologies such as ionomics, transcriptomics, proteomics, metabolomics or combinations thereof.

After phenotyping the SDR-1 progeny populations, the SDR-0 organism that gave rise to SDR-1 progeny populations that segregate are genotyped. Genotyping can be done by any method known to the person skilled in the art. In a preferred embodiment, genotyping of the SDR-0 organisms is performed by means of a method revealing nucleic acid polymorphisms. Many techniques revealing such polymorphisms are known, such as AFLP, RFLP, SNP, SFP, SSR, RAPD. This list of molecular marker techniques is only given as an example and is in no way limiting to the invention.

Advantageously, the production of the SDR-1 progeny population is performed under varying conditions, in particular varying environmental conditions. The varying environmental conditions are selected from laboratory conditions and field conditions. Both types of conditions can furthermore be varied with respect to weather conditions. This way it is possible to find and map traits that are phenotypically visible under certain conditions only.

In a further embodiment the same traits are mapped in different genetic backgrounds. This way it is possible to find interacting loci in one genetic background that are not visible in another genetic background.

The invention provides in fact the combination of a novel starting population and known QTL-mapping techniques. Because the level of heterozygocity in this population is much lower than in other populations the number of organisms that need to be analysed is much lower than in existent techniques. Moreover, in the most basic embodiment of the invention, only the SDR-0 organism that gives rise to a SDR-1 progeny population that segregates for the trait to be mapped need be genotyped in comparison to an SDR-0 organism the SDR-1 progeny population of which does not segregate for that trait. The locus responsible for the trait lies then within the heterozygous chromosome fragment present in the SDR-0 organism of the segregating SDR-1 progeny population.

Meiotic mechanisms have been described in considerable detail including a number of aberrant forms, which among others have been termed first division restitution or FDR and second division restitution or SDR. Both forms of meiosis lead to the formation of diploid gametes due to the absence of the first or the second meiotic cellular division, respectively. SDR leads to the presence of both sister chromatids in the spores/gametes, which therefore are identical with respect to their genetic composition except for those regions, which are heterozygous as a consequence of meiotic recombination (and which were thus also heterozygous in the donor-plant, which is the plant donating the SDR-0 spores).

In case of a single crossing-over per chromosome arm, the distal end of the chromosomes, i.e. from the crossing-over point towards the telomers, will be heterozygous whereas the chromosomal region proximal to the crossing-over point, which includes the centromere, will be homozygous.

Due to independent chromosome re-assortment during meiosis I, the homozygous regions of the chromosomes of the SDR events contain genetic information derived from either the paternally or maternally inherited chromosome and therefore an SDR population is very heterogeneous. Nevertheless, an SDR population could be described as a population that contains lines that resemble partly heterozygous RILs or HIFs, and partly heterozygous backcross inbred lines (BILs), the latter with introgressions in both parent backgrounds.

The occurrence of SDR spores/gametes is in itself well known and is described for several species (see e.g. Ki-Byung Lim et al. (2004) *Breeding Science* 54: 13-18; Veilleux R. (1985) *Plant Breeding Reviews* 3, 253-288;

Bastiaanssen H. (1997) Marker assisted elucidation of the origin of 2N-gametes in diploid potato (PhD thesis) ISBN 90-5485-759-5 (This thesis also includes references for many crops)).

Until now complex loci could not or hardly be genetically located by methods known to the person skilled in the art. The present invention teaches a completely new method for making mapping populations that allow scanning the whole genome for loci that segregate. The type of locus(ci) is (are) not limited to polygenic traits because the systematics can also be applied for monogenic traits.

The invention provides a novel and surprisingly simple way of analysing loci that may have interdependent and/or epistatic interactions. Moreover, the method is not limited to only 2 loci but can be applied to numerous loci that interact as long as intra-line segregation can be measured or observed.

Inter-line variability is well known to occur between fully homozygous lines (e.g. doubled haploids), whereas intra-line variability refers to the situation in which a limited number of phenotypic characters differ among individual plants within the line, due to segregation of the remaining heterozygosity in the line parent.

According to the invention it is surprisingly found that plants which are regenerated from spores that have omitted the second meiotic division, so called SDR-0 plants, provide unique material for mapping traits including extremely complex ones, such as those traits that are dependent on the presence of polygenic loci at various allelic configurations and effects such as heterosis.

The combination of the identification, enrichment or induction of unreduced spores of the SDR type, the subsequent regeneration of such spores into plants (SDR-0) and the molecular characterization of the SDR-0 plants (identification of the residual heterozygous chromosomal segments) and the correlation/association of such segments with the segregation for whatever trait or effect in the SDR-1 generation, and the comparison between different heterozygous SDR-0 lines and their segregational pattern, allows to map and identify all loci that either do or do not interact, whether polygenic or not.

Identification and localisation of the crossing-over breakpoints in the individual SDR-0 plants predicts and by consequence maps the position of the locus that is responsible for the segregation of a particular phenotypic trait in the SDR-1 progeny. In addition, fine mapping automatically takes place dependent on the number of regenerated SDR-0 plants and depending on the size of the genetic map.

BRIEF DESCRIPTION OF THE DRAWINGS

The present invention will be further illustrated in the non-limiting examples that follow and that refer to the following figures:

FIGS. 3A, 3B-1, 3B-2, 3B-3, 3B-4 and 3B-5 show the formation of spores/gametes that occur in the plant that is regenerated from SDR-0 event 3 in FIG. 2.

FIG. 4 shows theoretical individual SDR-0 plants (for one chromosome) that only differ in the extent to which recombination took place.

FIG. 5 shows AFLP patterns of typical F2 lines in cucumber. Every horizontal line represents one individual plant. Every vertical column represents a linkage group. Light grey segments represent heterozygous areas, whereas black and dark areas represent respective homozygous areas.

DETAILED DESCRIPTION

Figure 3A:
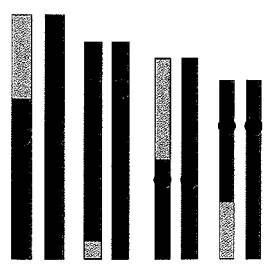
Figure 3A:
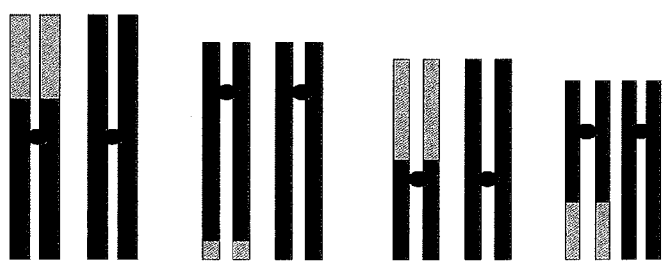
Figure 3A:
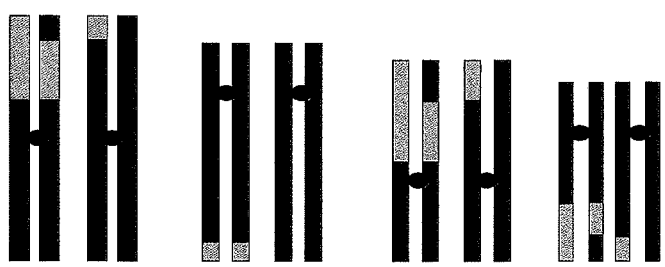
Figures 1, 3B:
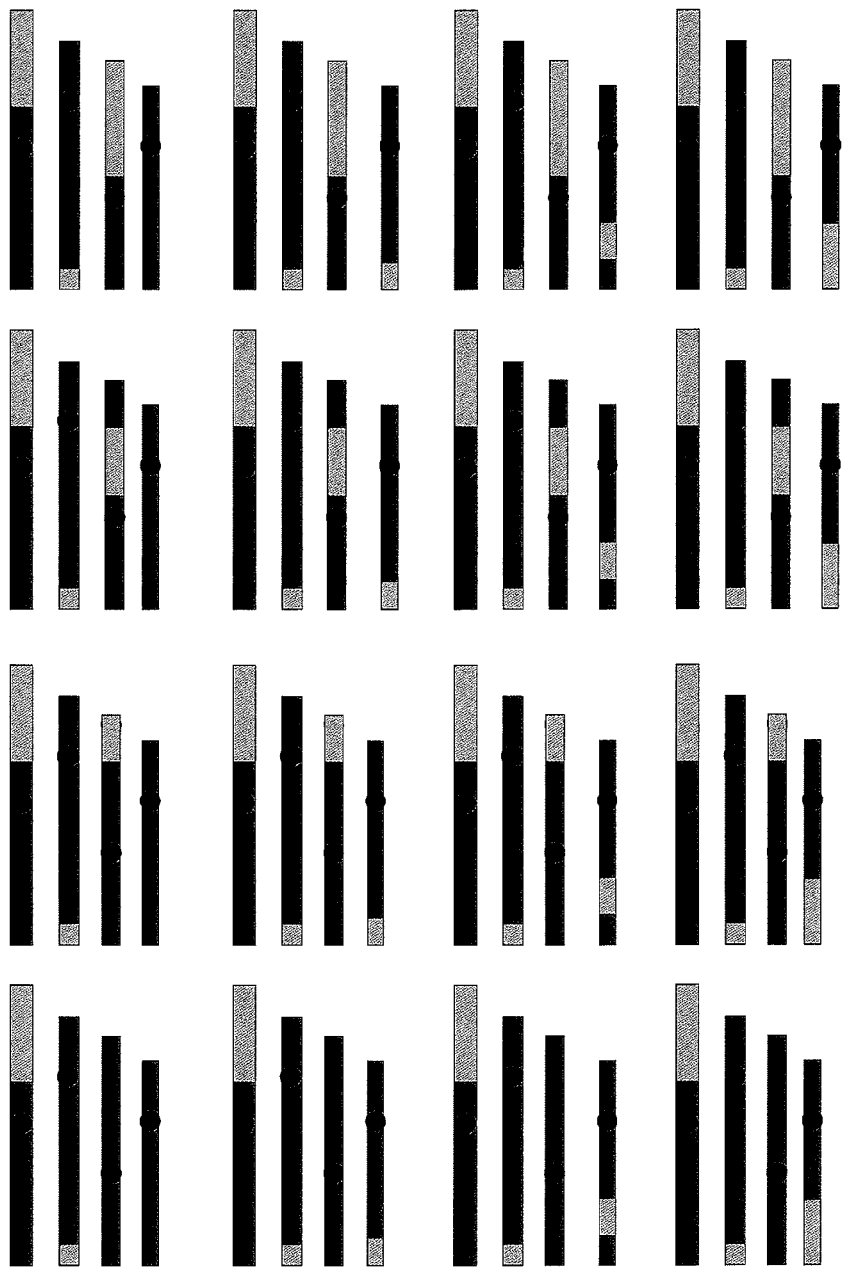
Figures 2, 3B:
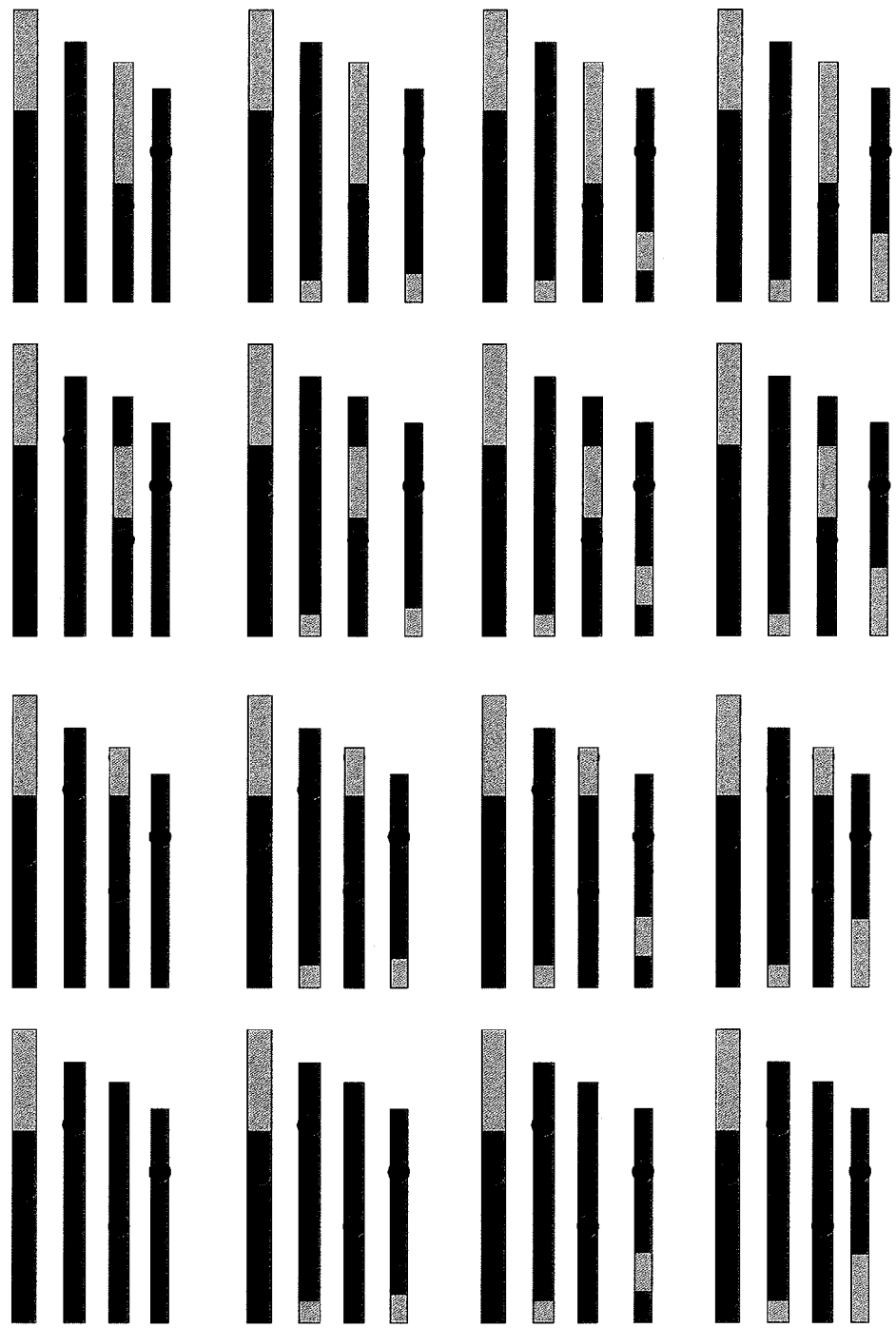
Figures 3, 3B:
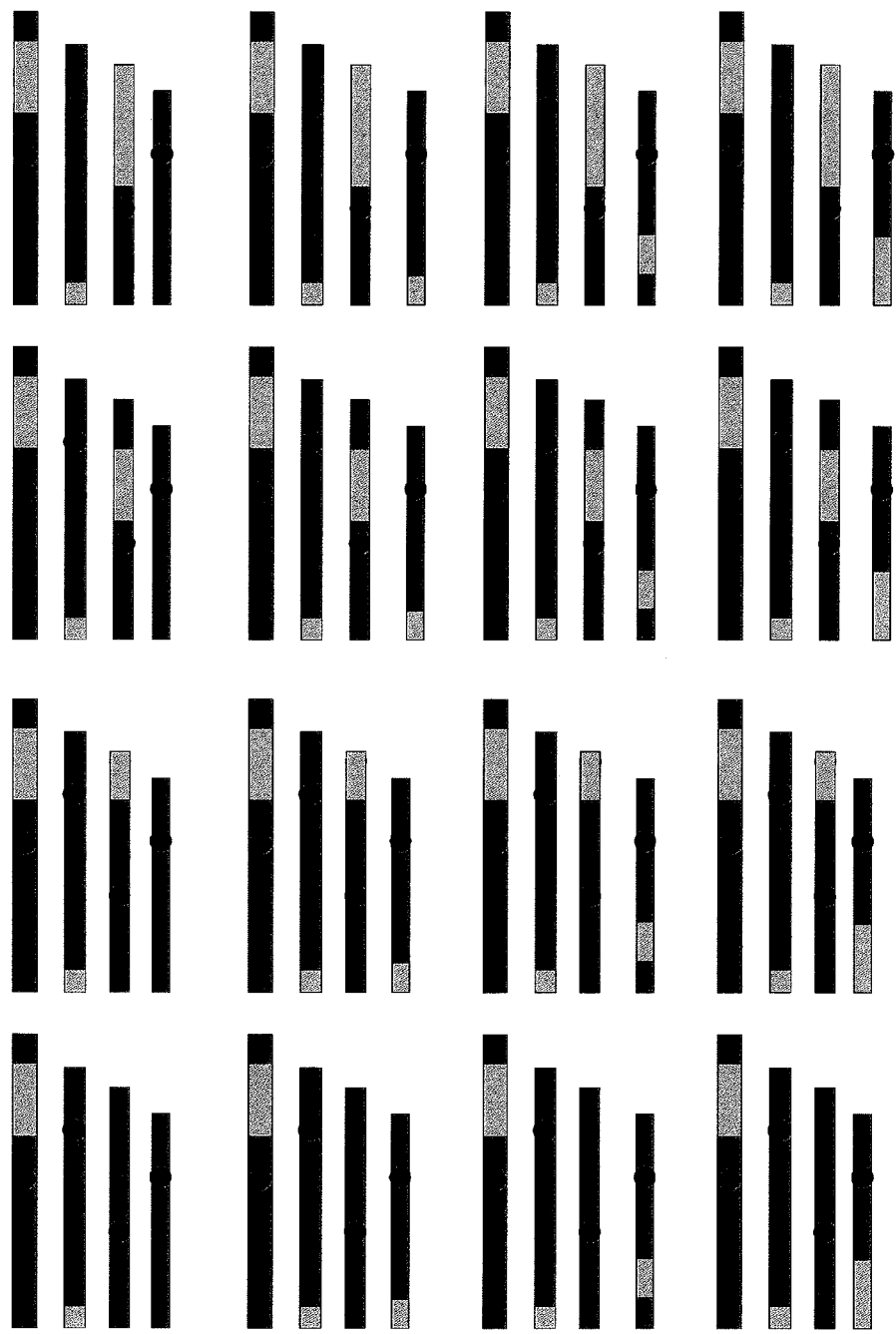

In greater detail, FIG. 1 depicts the occurrence of a normal meiosis for 4 chromosome pairs of a completely heterozygous hybrid and the spontaneous doubling of the chromosomes after the reduction division took place (named "corresponding Doubled Haploids"). In the case depicted crossing-over has led to the occurrence of 2 parental chromosomes and 2 recombinants chromosomes per set. Due to the combination of the individually different homologs from the different chromosome sets, many different spores/gametes can be produced. In FIG. 1 only 3 possibilities are depicted.

Doubled haploids (DH) plants are generated from such "spores". The production of doubled haploids is a well established technology (Doubled haploid production in crop plants, Ed: M. Maluszynski, K. Kasha, B. Forster and I. Szarejko. Kluwer Academic publishers, Dordrecht/Boston/London, (2003) ISBN 1-4020-1544-5).

Figure 1A:
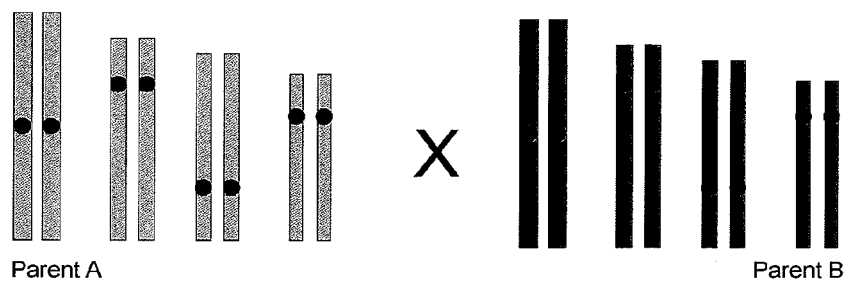
FIGS. 1A and 1B show the occurrence of a normal meiosis for 4 chromosome pairs of a completely heterozygous hybrid and the spontaneous doubling of the chromosomes after the reduction division took place (named "corresponding Doubled Haploids").
Figure 1A:
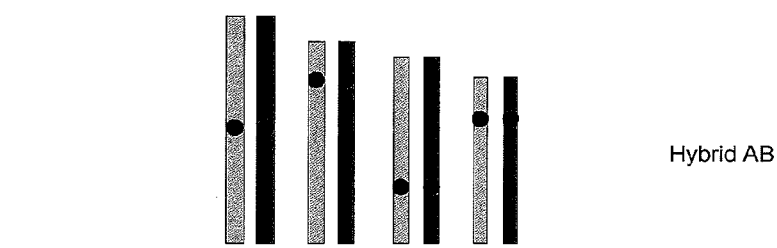
Figure 1A:
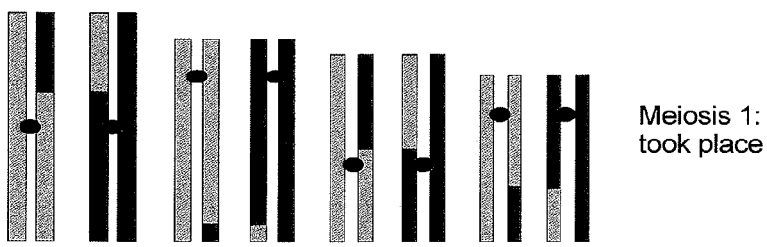
Figure 1B:
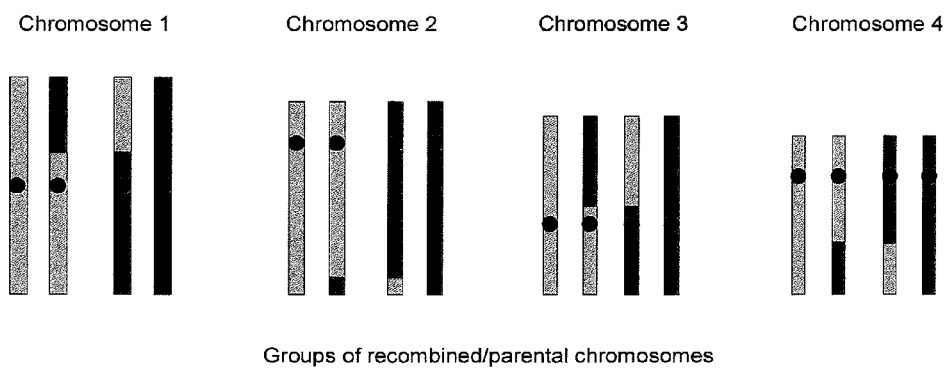
Figure 1B:
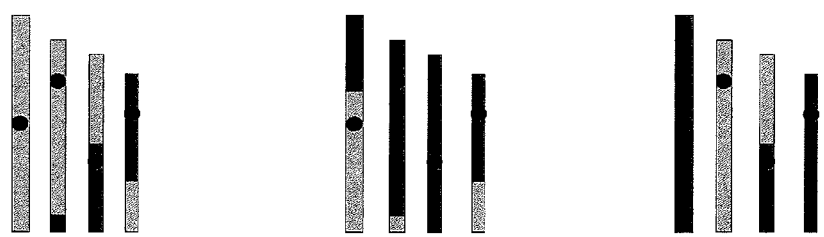
Figure 1B:
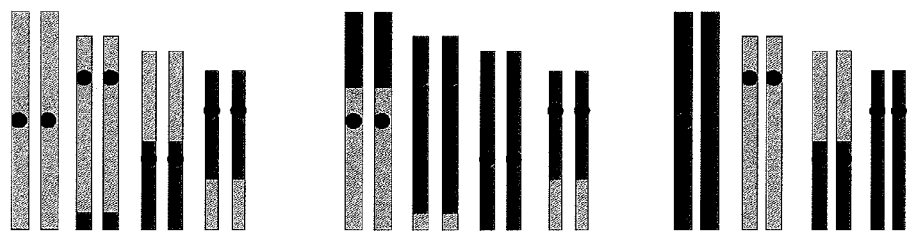
Figure 2:
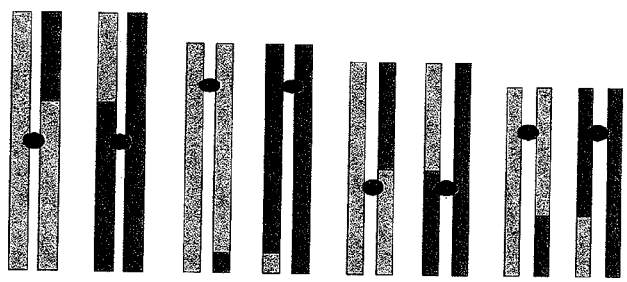
FIG. 2 shows a meiosis of the same heterozygous hybrid as in FIG. 1, but in the situation where the second division fails to take place (i.e. in case of Second Division Restitution). Note that in the $3^{rd}$ and $4^{th}$ example the basic make up of the chromosome sets are derived from the respective parents; such sets resemble "BIL's" but in heterozygous state. Examples 1 and 2 resemble "RIL's" in a heterozygous state.
Figure 2:
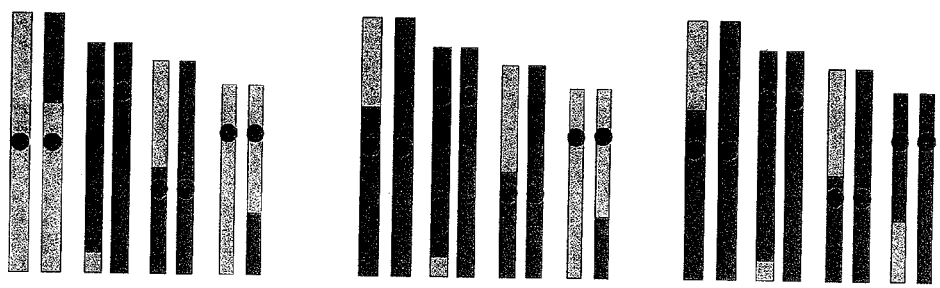
Figure 2:
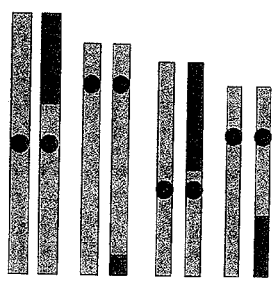

FIG. 2 depicts a meiosis of the same heterozygous hybrid as in FIG. 1, but in the situation where the second division fails to take place (i.e. in case of Second Division Restitution). In this particular case, diploid spores are formed, however in contrast to FIG. 1 where a spontaneous or induced chromosome doubling took place the occurrence of diploid spores is caused by the absence of the second meiotic division. In both figures, four chromosome pairs have been depicted and the homologs are shown in light, respectively dark rod like structures where the black circles on the rods represent the centromeres.

The core difference between a doubled haploid plant and diploid SDR plants is clearly seen by the heterozygous segment on the chromosomes in the SDR plant whereas the DH plant is fully homozygous.

In this theoretical case, the starting plant (donor-plant hybrid AB) that produced the haploid spores from which DHs were made or that produced SDR-0 spores, respectively, contains homologous chromosomes that are completely heterozygous. This means that all alleles of the genes carried by those chromosomes are different. In practice, however, this is highly unlikely and so this case exemplifies the most extreme heterozygous situation.

From FIG. 2 it is also clear that what determines the ratio of homozygous loci versus heterozygous loci in the case of SDR is the extent to which the non-sister chromatids of the homologous chromosomes have been exchanged due to crossing-over. The limit of cross-over extent for each chromosomal arm is determined by the position of the centromere. Of course cross-over from the other end of the chromosome can also take place and also in this case up to the centromere. Starting from plants which are 100% heterozygous, which means all alleles of the genes carried on the chromosomes are polymorphic, is an extreme situation. In practice this is highly unlikely to occur and therefore the percentages of heterozygocity of the starting plants will on average be lower.

Note also in FIG. 2 the occurrence of SDR-plants that resemble RILs and BILs. In the case of BIL-look-alikes the centromeres are all descending from one and the same original parent, i.e. A or B (see FIG. 1).

Plants regenerated from haploid spores originating from a normal meiotic event in which the chromosome number has been doubled spontaneously or by means of chemicals will be further named DH-0. Plants will be called SDR-0 in case the primary regenerant originates from a spore that resulted from a meiotic event that lacked the second meiotic division.

DH-0 plants when self-pollinated will give rise to a progeny (DH-1) that is genetically 100% identical and is completely fixed in all the alleles. So although the spores (gametes) that are formed on the DH-0 plants underwent again meiosis and recombination no genetic rearrangements can take place. This means that this so-called "pure line" is immortalized because no segregation can take place.

Such a pure line can, however, phenotypically show different appearances when grown under different conditions, such as low or high temperatures, or for instance in different climatic zones. The differences that can be observed are due to environmental variation and valid for all "members" of the line. In other words there will be no "intra-line" variation. The difference between plants of different DH1-lines descending from different DH-0-plants has a genetic basis and is indicated as "inter-line" variation.

In the case of SDR a different picture is observed in the SDR-1 generation. FIGS. 3A and 3B depict the formation of spores/gametes that occur in the plant that is regenerated from SDR-0 event 3 in FIG. 2. It is clear from FIG. 3B that by recombination and combination a panoply of chromosome combinations can occur and obviously the number of combinations increases as the number of chromosomes increases. To find a (partially heterozygous) BIL-look-alike for one of both inbred parents, the probability is $(½)^{x-1}$ where x is the number of chromosomes. To find a specific (partially heterozygous) BIL-look-alike the probability is $(½)^x$. The maximum variation that is phenotypically observable is dependent of the extent of heterozygosity in the starting material and also on the extent of recombination that took place. In the unlikely situation where no recombination took place at all, or only in homozygous regions, the SDR-0 regenerant will both genotypically and phenotypically be the equivalent of a doubled haploid (DH-0).

Figures 3, 3B, 4:
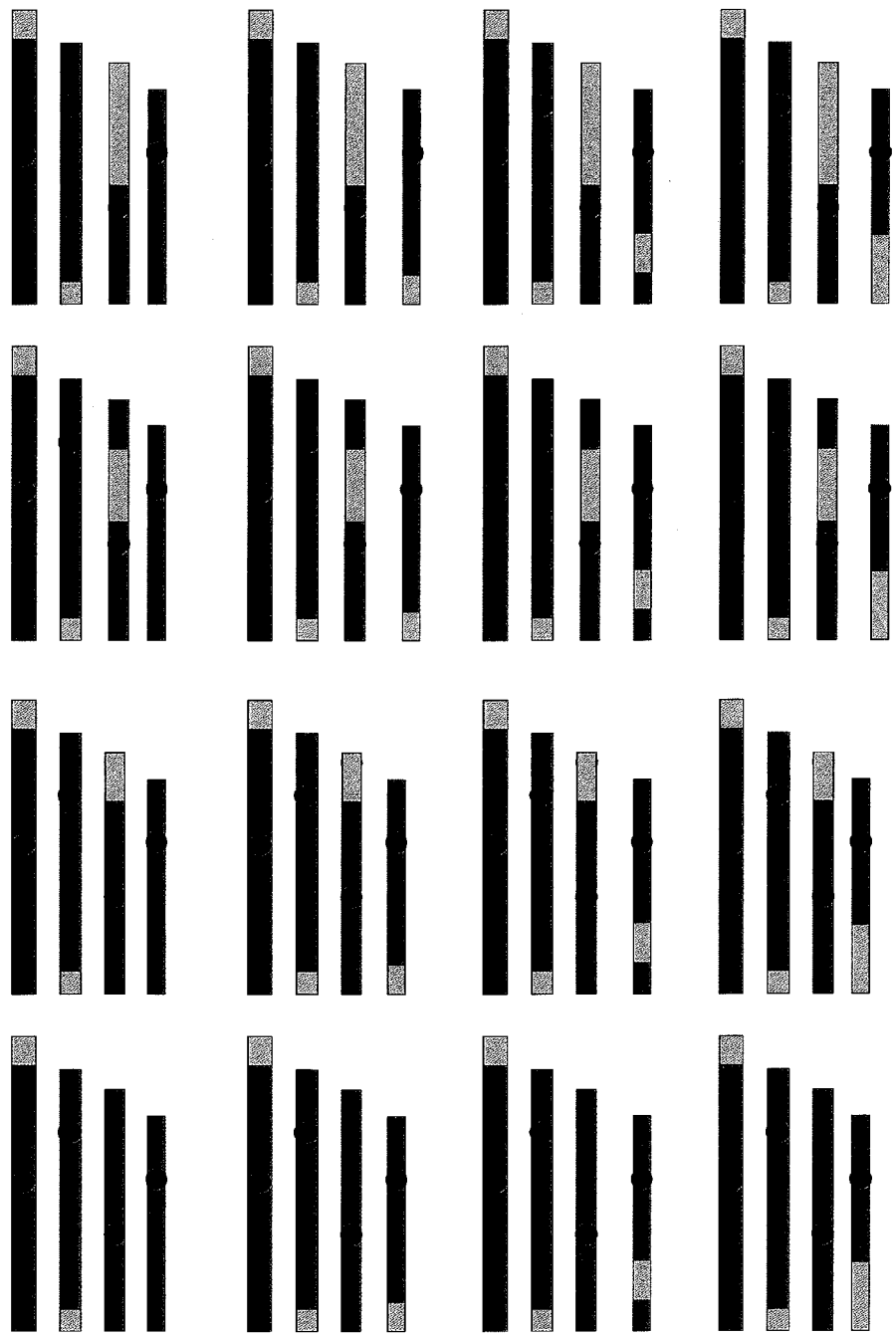

FIG. 4 shows theoretical individual SDR-0 plants (for one chromosome) that only differ in the extent to which recombination took place. In case segregation for a trait or effect is seen in the SDR-1 generation for SDR-0 C but not in the A and B case, then it follows that the chromosomal region responsible for the segregation is located between the cross-over positions of B and C. Depending on the availability of molecular markers and the number of available SDR-0 plants, loci that are responsible for segregating phenotypes can thus be very accurately mapped and associated with known molecular markers.

This method of the present invention is called herein "reverse progeny mapping". The unique feature of this method is that it is using intra-progeny segregation information of plant progenies from a mapping population of parent plants to perform QTL-mapping. In contrast to the use of the progeny means, which is often used in traditional mapping, the method makes use of the progeny variation. It is using the contrast between the individuals that are heterozygous for a certain chromosome position and the individuals that are homozygous for a this position, irrespective for which parental allele. Traditional methods make use of the contrast between all three allelic states of a chromosomal position (homozygous parent (AA), heterozygous (AB); homozygous parent (BB)), with an emphasis on the contrast between the two homozygous states.

In another embodiment, reverse progeny mapping can be combined with regular inter-line mapping methods to increase the power of QTL-detection.

In a further embodiment, individual SDR-1 plant phenotypes can be used in a general mixture model approach (Jansen R C (1992) *Theor. Appl. Genet.* 85: 252-260), where the three possible allelic states are modelled for each SDR-0 individual, that is heterozygous on the analysed chromosome position.

Alternatively, it is possible to use SDR-1 line variance, for example to calculate an additional likelihood ratio, which can be multiplied with the regular likelihood ratio, for inter-line mapping, to obtain an improved test statistic.

In another embodiment, it is possible to use simply the score for presence or absence of segregation in an SDR-1 line. Also in this case, an additional likelihood ratio may be calculated.

The above examples do not exclude other possibilities to combine the use of intra-line and inter-line segregation of the invention with another technique for QTL-mapping.

There are certain conditions in which the method of reverse progeny mapping works optimally. In a preferred embodiment the trait, for which QTLs should be mapped, is segregating in only part of the SDR-1 lines, preferably between 50 and 80%. This means that for certain polygenic traits, for which a higher number of QTLs are segregating in the population, a lower level of heterozygosity is required. If necessary this can be achieved by further inbreeding in the case of HIFs, or in the case of SDR, by a second round of SDR, where each SDR-0 individual is used to produce a new SDR-0 plant, resulting in a so called $SDR^2$-0 population. Care should be taken that the population size is large enough to have the whole genome still represented in a heterozygous state.

According to the present invention SDR-0-based Reverse Progeny Mapping (RPM) combines the ideal characteristics of doubled haploid lines in phenotypic recording and the possibility to assess the effect of heterozygous loci individually and in interaction with other heterozygous or homozygous loci.

As already stated earlier, SDR lines are different from DH lines in those chromosomal regions where they are heterozygous as a consequence of heterozygosity in the starting material and due to recombination at those heterozygous segments. This means that for all the other segments SDR lines resemble DH-lines. This means that at a phenotypic level within-line segregation is observed for only a limited number of characteristics. Nevertheless, the phenotypic classes which require heterozygosity of specific loci may be recorded. If, for instance, a locus which determines a specific trait, is heterozygous in the SDR-0 generation, it may give a traditional Mendelian segregation of 1:2:1 (AA:Aa:aa) in the SDR-1 generation depending on the recombination position in the second round of gamete formation. If the Aa phenotype is different from AA and aa, then still it can be recorded.

In the theoretical case where a certain locus has to be in a heterozygous state to be fast growing, SDR-1 lines descending from the SDR-0 plants that have this locus in a heterozygous state, will show a 1:1 segregation of faster growth versus normal growth, provided that the second round of recombination did not change the recombination position of the SDR-0 plant. This is a clear example of the application of "intra-line variation" in SDR-0 lines, as opposed to "inter-line variation" that occurs between DH-1 lines.

Again, the segregation for the theoretical "fast growth" characteristic can be explained by the presence of heterozygous segments in the SDR-0 generation. So it is sufficient to genetically analyse the SDR-0 generation to explain and map what phenotypically happens in the SDR-1 generation.

The power of the method of the invention is also demonstrated by the fact that interaction between independent loci can be explored. As an example, a plant is considered in which one locus should be homozygous recessive (aa) while two other loci should be heterozygous to show the trait of interest. In this case, no segregation will take place for the trait of interest if the SDR-0 generation was AA. But if the SDR-0 generation was aa then still the trait may segregate for the other loci. Such so-called epistatic effects are difficult to study especially if the trait is also dependent on the environment.

The advantage of phenotypic recording of DH populations is nullified by the lack of segregation within the line, and the lack of heterozygosity of DH-plants. An F2-population will, however, show the desired segregation of the trait, but analysis is hampered by the fact that the whole genome is segregating, providing each of the F2-individuals with a different genetic background. This is creating a large statistical background noise which decreases the power of detecting the epistatic QTL-effect. In addition to that, the F2-plant can only be phenotyped once, which introduces an large environmental error. The possibility to replicate a DH line in different environments and record the phenotypic differences several times, is a big advantage for reliable QTL-mapping.

The same is true with the method of the invention. When sufficient seeds are produced from the SDR-0 lines to allow to test the same SDR-1 generation in different conditions, not only loci that contribute in a homozygous state but also loci that perform different in a heterozygous state can be recorded.

noted in the table. It is clear from the table that in comparison with other populations creating SDR-based populations requires limited time and input, with the prospect of remarkably good results. In this way the SDR-approach combines the advantages of doubled haploid populations (DH), i.e. quick population development at limited cost, with the QTL-mapping potential of heterogeneous inbred families (HIFs), i.e. reliable phenotyping, strong detection power of QTLs, including their heterozygous and epistatic effects, and potential for fine mapping.

TABLE 1

| | EFFORTS | | | | RESULTS | | | | | |
|---|---|---|---|---|---|---|---|---|---|---|
| POPULATION TYPE | labour to produce population | time to produce population | number of markers required (rough mapping) | population size required (rough mapping) | number of QTL-alleles per locus | reliability of phenotype | QTL-detection power | estimation of QTL-effect for heterozygote | fine mapping (number of recombinations and/ or residual heterozygosity) | analysis of epistasis |
| F2 | ** | ** | * | * | 2 | $--/-^{6,8}$ | - | = | - | + |
| BCx | */*[3] | */*****[3] | */[3] | [5] | 2 | = | + | + | = | - |
| RIL | **** | **** | *** | * | 2 | $++^{7}$ | ++ | - | + | $++^{12}$ |
| HIF | ***** | ***** | *** | * | 2 | $+^{8}$ | ++ | + | ++ | +++ |
| BIL[1] | ***** | ***** | ** | * | 2 | $++^{7}$ | ++ | $+^{9}$ | $++^{9}$ | - |
| DH | *** | ** | * | * | 2 | $++^{7}$ | ++ | - | - | $++^{12}$ |
| SDR | *** | ** | * | * | 2 | $+^{8}$ | ++ | + | ++ | +++ |
| random[2] | * | * | *****[4] | *** | >=2 | $++^{7}$ | = | $+^{10}$ | $-/+^{11}$ | = |

Overview of required efforts to create and use several population types for QTL-mapping and potential results.
Efforts (costs/time frame):
*: very limited, : limited, *: average, **: large, ***: very large;
Results (except for: estimation of QTL-effect for heterozygote): --: very poor, -: poor, =: moderate, + = reasonable, ++ = good, +++ = very good;
Results (only for: estimation of QTL-effect for heterozygote): -: impossible, =: possible, +: good.
BCx: backcross population after x cyles of backcrossing;
RIL: recombinant inbred lines;
HIF: heterogeneous inbred families;
BIL: backcross inbred lines;
DH: doubled haploid lines;
SDR: second division restitution derived lines.
[1]See for instance: Jeuken M J W, Lindhout P (2004): The development of lettuce backcross inbred lines (BILs) for exploitation of the *Lactuca saligna* (wild lettuce) germplasm; Theor. Appl. Genet. 109(2): 394-401/
[2]Populations of breeding lines, varieties, genebank accessions, used for f.i. LD-mapping
[3]Effort is increasing with the number of backcross generations (x)
[4]High numbers of markers required for haplotyping multiple alleles
[5]Higher number required for sufficient genome coverage, especially in higher backcross generations
[6]F3-line phenotyping is more reliable than F2-plant phenotyping
[7]Unlimited replication possible
[8]Limited replication possible, depending on seed quantity per line
[9]Possible via cross with recurrent parent
[10]Only in case of hybrids
[11]Depending on degree of linkage disequilibrium in population
[12]Only QTL-interactions between homozygous loci Additionally, recording is possible for epistatic interactions between loci whether heterozygous or homozygous, and of course for monogenic loci encoding qualitatively or quantitative traits. This is a clear advantage over the existing techniques.

Map distances on chromosomes are expressed in centimorgan (cM) as is well know to the person skilled in the art. In a 100 centimorgan interval, an average of one crossover occurs per chromatid (Van den Berg J et al. (1997) pp. 334-396 in: *Plant molecular biology—a laboratory manual*, Ed. M. Clark, Springer Verlag, Berlin). This means that if one is looking for mapping a trait which is positioned at 1 cM from the centromere, there is 1 in 50 recombinants that has a chromatid exchange up to 1 cM from the centromere. This applies, of course, to either side of the centromere.

In Table 1 the advantages and disadvantages of using certain population types for QTL-mapping are summarised. Most of them have been mentioned before; otherwise they are Zhang X et al. ((2002) *Journal of Horticultural Science & Biotechnology* 78(1), 84-88) found that in pepper the frequency of SDR 2n gametes (pollen) could be increased from <1% to up to 10.5% (average) by 48 hours exposure of the plants to 11° C. The maximum SDR occurrence was measured to be 81.3%. This method can be used according to the invention to increase the number of SDR events and thus the number of SDR-0 gametes.

In addition to the spontaneous occurrence of SDR or induction of an increase in the number of SDR-0 events by environmental stress, different genetic approaches are provided, which allow interference with gene functions involved in the second cell division of meiosis. Such interference can either be through mutagenesis or transgenesis. Transgenic approaches aim at the stable or transient introduction of a DNA fragment which modifies the second division of meiosis leading to diploid spores of the SDR type. The modification can occur through interference with genetic factors involved in meiotic processes, especially those involved in the second cell division. The interference can be established through specific down-regulation of gene expression based on post-transcriptional gene silencing (PTGS). PTGS can be achieved through RNA-interference (RNAi) or virus-induced gene silencing (VIGS). The techniques for this are well known in the state of the art.

Yet in another approach, the interference can be established through the over-expression of proteins, which exert a dominant negative effect on the second division of meiosis leading to SDR.

Thus, in a first embodiment of the invention, the population of unreduced SDR-0 cells is produced by an organism selected to show an above-average second division restitution. Alternatively, the population of SDR-0 cells is produced by an organism that is genetically modified to show an above-average second division restitution. The genetic modification is transient or by stable incorporation into the genome of a genetic element increasing the number of second division restitution events in the organism.

In a still further embodiment, the population of unreduced SDR-0 cells is produced by an organism that is subjected to environmental stress to show an above-average second division restitution. Examples of environmental stress are temperature stress, $NO_2$, nitrous oxide $N_2O$, or combinations thereof.

The invention further relates to the use of a mapping population obtainable by the steps of:

a) providing a population of SDR-0 organisms, in particular plants, that each arise from one member of a population of unreduced cells resulting from second division restitution, in particular a population of unreduced spores; and b) producing SDR-1 progeny populations of each of these SDR-0 organisms; for mapping one or more traits in a species.

Irrespective of the approach taken, the target gene needs to be known at the molecular level. A number of recessive mutants have been described of potato (pcpc, osos, fcfc) and maize (elongate), which result in an SDR-type of meiosis. The genes, which have been mutated in these specific examples, have not yet been identified at the molecular level but are excellent candidates to achieve SDR in target species using molecular suppression technologies although they are not yet cloned. The present invention relates to the general principle of reverse progeny mapping and the fact that not all possible embodiments of inducing SDR in a donor organism have been described is not relevant for the invention.

Alternatives can be found in genes like DUET (Venkata Reddy et al. (2003) *Development* 130, 5975-5987) and CYC1; 2 (Wang et al. (2004) *Plant Physiology* 136, 4127-4135), which have been described in *Arabidopsis thaliana* and which upon mutation, lead to an aberrant meiosis. The diploid meiotic products in these mutants are SDR-like and therefore DUET and CYC 1; 2 as well as their functional homologues in other plant species are candidate target genes to achieve SDR meiosis.

Another candidate target gene is TETRASPORE/STUD (Yang et al. (2003) *Plant J.* 34, 229-240), which upon knock out leads to absence of cell division after meiosis. Diploid regenerants of microspores of a tetraspore/stud mutant can be SDR-like.

The occurrence of 2n spores or gametes is not restricted to the male gametophyte but there is also evidence that this occurs at the level of the female gametophyte. Zagorcheva L (1976), reported the occurrence of deviations of macrosporo- and macrogametogenesis in cucumber see: Macrosporgenesis and macrogametogenesis ((1976) *Genetics and Plant Breeding* 9(5) pp 386-399).

In addition, by making haploids and doubled haploids in cucumber according to EP 0 374 755 the inventors found by using AFLP analysis (carried out according to EP 0 534 858) that among the expected doubled haploids, a certain percentage did not originate from haploid megaspores but from an unreduced megaspore (2n). This is demonstrated in FIGS. 5, 6 and 7.

Figures 3, 3B, 4, 5:
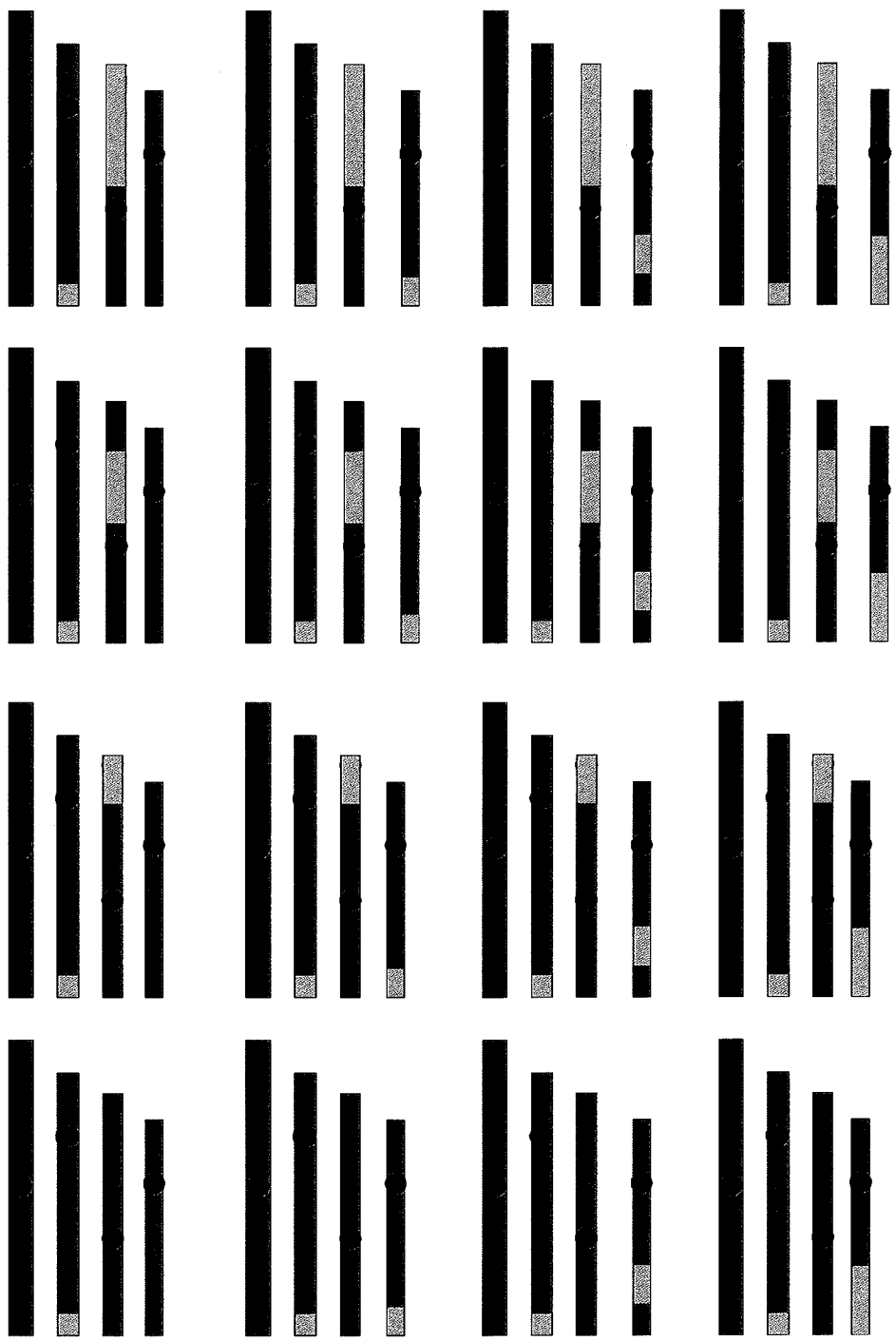
Figure 4:
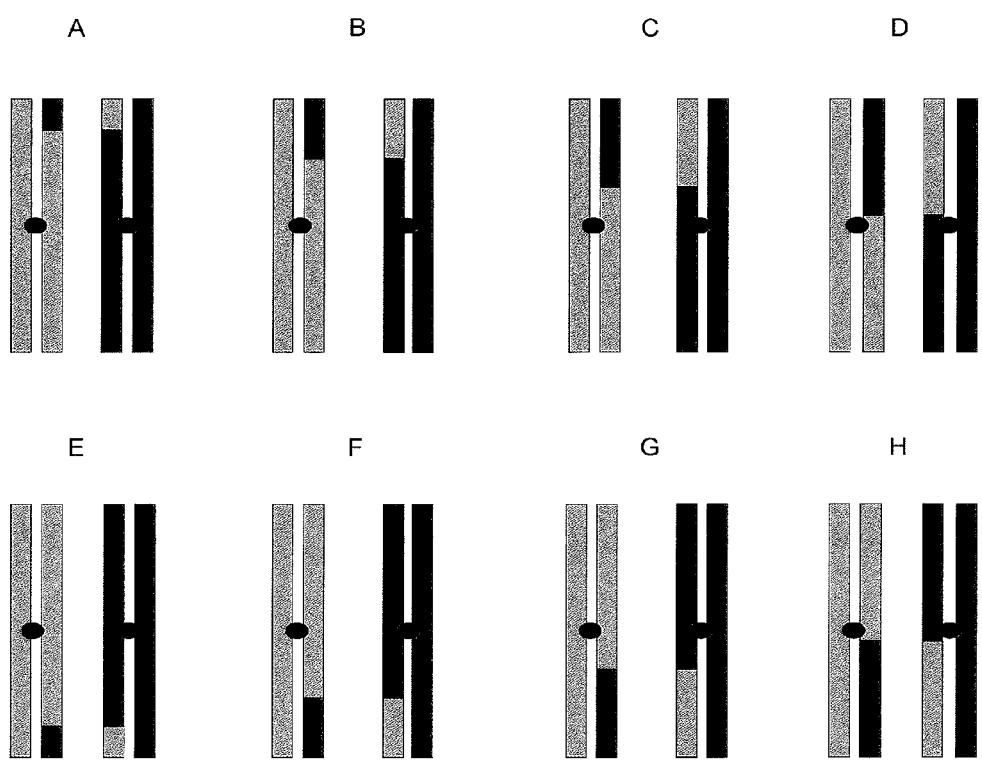
Figure 5:
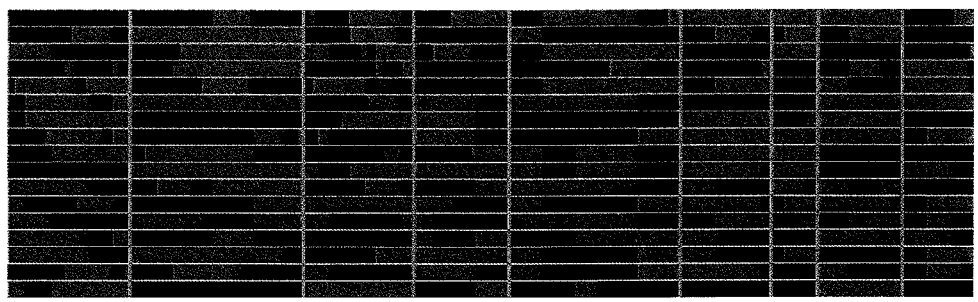

FIG. 5 shows AFLP patterns of a typical F2 lines in cucumber. Every horizontal line represents 1 individual plant. Every vertical column represents a linkage group. Light grey segments represent heterozygous areas, whereas black and dark areas represent respective homozygous areas.

Figure 6:
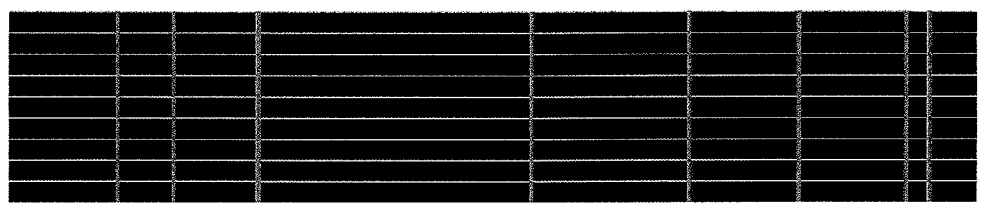
FIG. 6 shows AFLP analysis of typical DH lines in cucumber. Every horizontal line represents one individual plant. Every vertical column represents a linkage group. Only black and dark areas are present as expected in DH's Light grey segments are absent.

FIG. 6 shows AFLP analysis of typical DH lines in cucumber. Every horizontal line represents 1 individual plant. Every vertical column represents a linkage group. Only black and dark areas are present as expected in DH's Light grey segments are absent.

Figure 7:
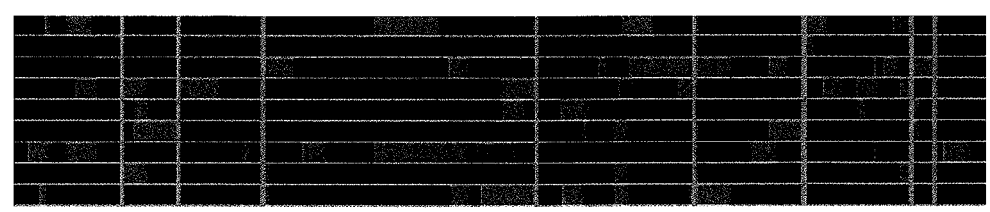
FIG. 7 shows the AFLP analysis of typical SDR-0 plants in cucumber. Every horizontal line represents one individual plant. Every vertical column represents a linkage group. Light grey segments represent heterozygous areas, whereas black and dark areas represent respective homozygous areas. It follows from comparison of these figures that the heterozygosity in these plants is much lower than in an ordinary F2.

FIG. 7 shows the AFLP analysis of typical SDR-0 plants in cucumber. Every horizontal line represents 1 individual plant. Every vertical column represents a linkage group. Light grey segments represent heterozygous areas, whereas black and dark areas represent respective homozygous areas. It follows from comparison of these figures that the heterozygosity in these plants is much lower than in an ordinary F2.

The figures thus show that the originally presumed doubled haploids (FIG. 7) still contain heterozygous sectors, which by definition is not possible in true doubled haploids (FIG. 6). For comparison FIG. 5 shows the AFLP analysis of a typical F2 population.

Depending on the amount of polymorphism of the starting material, unreduced spores/gametes and plants thereof may be obtained that contain only one or a very limited number of heterozygous segments. If in such case there is a causal relationship between the segregating trait in the SDR-1 generation and the position of the heterozygous segment, in the SDR-0 plant, mapping is very easy and fine mapping can be undertaken in order to even decrease the size of the heterozygous segment by methods known by the person skilled in the art.

In order to obtain SDR gametes, one can use a number of different approaches. In many species diploid gametes are produced spontaneously, both on the male and female side, which may be enhanced by specific stress conditions. Regeneration may occur through androgenesis, gynogenesis or parthenogenesis by prickle pollination. Optimisation may be carried out by pollination using diploid pollen and determination of the ploidy level of the offspring.

When SDR meiocytes are produced through male meiosis it is possible to enrich for diploid cells through flow cytometry and fluorescence activated cell sorting. Such technologies are per se well known to the person skilled in the art and have been applied on microspores in the past (see e.g. Deslauriers C et al. (1991) *Biochem. Biophys. Acta* 1091, 165-172) but these techniques have not yet been used in a mapping method of the invention.

Figure 8:
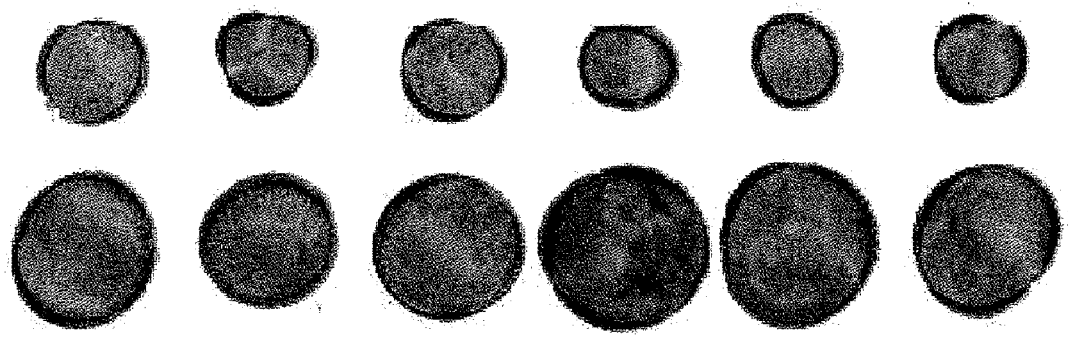
FIG. 8 shows the result of an experiment where broccoli microspores from a tetraploid plant (giving diploid (2n) spores) were mixed with microspores from a diploid plant (giving haploid (n spores). The larger spores are 2n.

Unreduced spores or pollen are bigger than their haploid peers. Surprisingly, the mere fact that 2n spores are physically different from n spores makes it possible through flow cytometry to enrich specifically for 2n spores. FIG. 8 shows the result of an experiment where broccoli microspores from a tetraploid plant (giving diploid (2n) spores) were mixed with microspores from a diploid plant (giving haploid (n) spores). The larger spores are 2n.

Thus, according to a further aspect thereof, the invention provides a method for enrichment of a population of cells, in particular spores or gametes, for SDR cells, in particular SDR spores or gametes, comprising sorting the population of cells, in particular spores or gametes, on the basis of size, mass or DNA content and selecting the cells, in particular spores or gametes, that have an increased size, mass or DNA content as unreduced cells, in particular unreduced spores or gametes. In a specific embodiment, the invention provides a method for enrichment of a population of spores or gametes for SDR spores or gametes, which method comprises sorting the members of the population of spores or gametes by means of a sorting device, in particular by means of FACS.

The invention thus relates to the use of plants and their progenies, regenerated from SDR or SDR-like unreduced gametes for the purpose of mapping polygenic traits or effects, for the mapping of quantitative traits or effects, for mapping loci that are interdependent, for mapping loci that show epistatic interactions, for mapping effects as heterosis, respectively combining ability and for mapping of mono- or oligogenic traits.

The present invention has been described herein referring in particular to plants, but the technology is not limited to plants but can also be used for mapping traits in other organisms, such as fungi or animals. Animals may be, for example, fish, birds, reptiles, or mammals.

When the term "unreduced cells" is used in this application "unreduced reproductive cells", such as spores or gametes, are intended.

The present invention will be further illustrated in the Examples that follow and that are not intended to limit the invention in any way.

EXAMPLES

Example 1

Production of SDR-0 Organisms in Maize by Means of Introduction of Elongatel

Incorporation of nucleic acids in the genome of maize are routine procedures and methods how to achieve this have been described in e.g. EP-801134, U.S. Pat. No. 5,489,520. EP-97114654.3 teaches *Agrobacterium* transformation of DSM6009 corn protoplasts.

Elongatel (Barell, P J and Grossniklaus, U. (2005) Plant J. 43, 309-320), a nucleic acid sequence that disturbs meiosis resulting in the omission of the second meiotic division was introduced into maize using the transformation methods described in the above patent publications. Thus, aberrant spores of the SDR type were obtained. The frequency of SDR spores that are formed sometimes differed between independent transformants as a consequence of different genomic sites of integration of the transgenic nucleic acid sequences.

The microspores or megaspores which were produced as a consequence of an SDR-event contain a diploid set of chromosomes. These diploid microspores or megaspores were the starting material for producing SDR-0 regenerants. Haploids in maize were routinely obtained from microspores: Pescitelli S and Petolino J (1988) Plant Cell Reports 7: 441-444. Coumans M et al., (1989) Plant Cell Reports 7: 618-621. Pescitelli S et al., (1989) Plant Cell Reports 7: 673-676. Buter B (1997) In vitro haploid production in maize. In: In Vitro Haploid Production in Higher plants, vol 4, 37-71. Kluwer Academic Publishers. Eds. S Jain, S Sopory & R Veilleux.

Alternatively, haploid maize plants were obtained following natural and artificial pollination with a haploid inducer. In this case seeds were obtained that contain haploid embryos according to Rotarenco V (2002) Maize Genetics Cooperation News Letter 76: 16.

The above protocols to produce DH maize plants were also applied to produce SDR-0 maize embryos from SDR-0 cells, of which the formation is induced by incorporation of Elongatel into the genome.

In order to obtain the proper balance between the maternal and paternal genomes at the level of endosperm of the SDR-0 kernels, preferably the inducer line is used as a tetraploid pollinator.

Example 2

Production of SDR-0 Organisms in Maize by Low Temperature or Nitrous Oxide Gas Treatment The frequency of SDR spores was enhanced by treatment of maize plants with low temperatures or by applying nitrous oxide gas as described by Kato, A and Birchler, J A (2006) J. Hered. 1, 39-44.

As a consequence of application of low temperatures or nitrous oxide treatments, numerous microspores respectively megaspores, were produced which are of the SDR-type. The spore population was enriched for the presence of SDR microspores by using flow cytometry or fluorescence activated cell sorting based on the fact that SDR microspores are larger in size as compared to normal haploid microspores. The microspores or megaspores which were produced as a consequence of an SDR-event contain a diploid set of chromosomes. These diploid microspores or megaspores are the starting material for producing SDR-0 regenerants. Haploids in maize were routinely obtained from microspores as described in Example 1.

Haploid maize plants were also obtained following natural and artificial pollination with a so-called haploid inducer. In this case seeds were obtained that contained haploid embryos according to Rotarenco V (2002) (supra).

The above protocols to produce DH maize plants were applied to produce SDR-0 maize plants from SDR-0 cells, of which the formation is induced by the treatments specified in this example.

As mentioned in Example 1, preferably use is made of the so-called haploid inducer as a tetraploid pollinator in order to balance paternal and maternal genomes at the level of endosperm.

Example 3

Identification and Characterization of SDR-0 Organisms

The SDR-0 maize plants from Examples 1 and 2 can be distinguished from DH plants (or from FDR (first division restitution) plants) that did not undergo SDR because they are partially heterozygous but have homozygous centromeric regions. Using the AFLP analysis as described in Example 5 for cucumber, DH-0 maize plants that did not undergo SDR will show an AFLP marker pattern without heterozygous areas, while DH maize plants that have undergo SDR will show heterozygous areas in the AFLP marker pattern. Subsequently, map construction and statistical analysis was performed as described in Example 5 for cucumber.

Example 4

Analysis of SDR-1 Populations and Fine-Mapping of Traits in Maize

The progeny of each of the SDR-0 plants carrying heterozygous regions in their genome was observed under uniform conditions and segregating progenies were classified according to the trait that segregates. The SDR-0 plants leading to the SDR-1 progenies segregating for a specific trait are compared with each other and with lines that do not segregate for that trait. Segregation in the SDR-1 generation may be associated with the heterozygous segments of the genome of SDR-0 plants. This was verified by means of a classical QTL analysis to determine the maximum-likelihood interval between the most flanking markers and the trait locus. Fine mapping of the locus that is responsible for the segregation in the SDR-1 generation was performed according to Peleman, J et al., (1995) Genetics 171:1341-1352.

Example 5

Production of and Identification of Heterozygous Segments for Mapping in Cucumber SDR-0 Plants 1. Doubled Haploids and SDR-0 Plants Doubled haploids and SDR-0 plants were regenerated from a F1 derived from a cross between 2 homozygous (pure) cucumber lines. All individual DH and SDR-0 plants were genotypically analysed by means of AFLP.

The production of doubled haploids and SDR-0 plants were carried out according to EP 0374 755.

2. AFLP Analysis

AFLP analysis on DH-0 and SDR-0 plants was performed as described by Vos P et al., (1995) Nucleic acids Research 23(21): 4407-4414.

The data were processed and analysed with Quantar Pro (Keygene, Wageningen, The Netherlands) allowing codominant scoring of the AFLP markers.

3. Map Construction and Statistical Analysis Genetic maps were calculated using the computer package JoinMap® version 2.0 (Stam, P., (1993) Plant J. 3: 739-744).

4. Segregation Characteristics

The following characters where expected to segregate.

Apex splitting

Leaf size

Growth rate

Number of fruits per node

Internode length

Flower size

Fruit size

Fruit colour

5. Results

Figure 10:
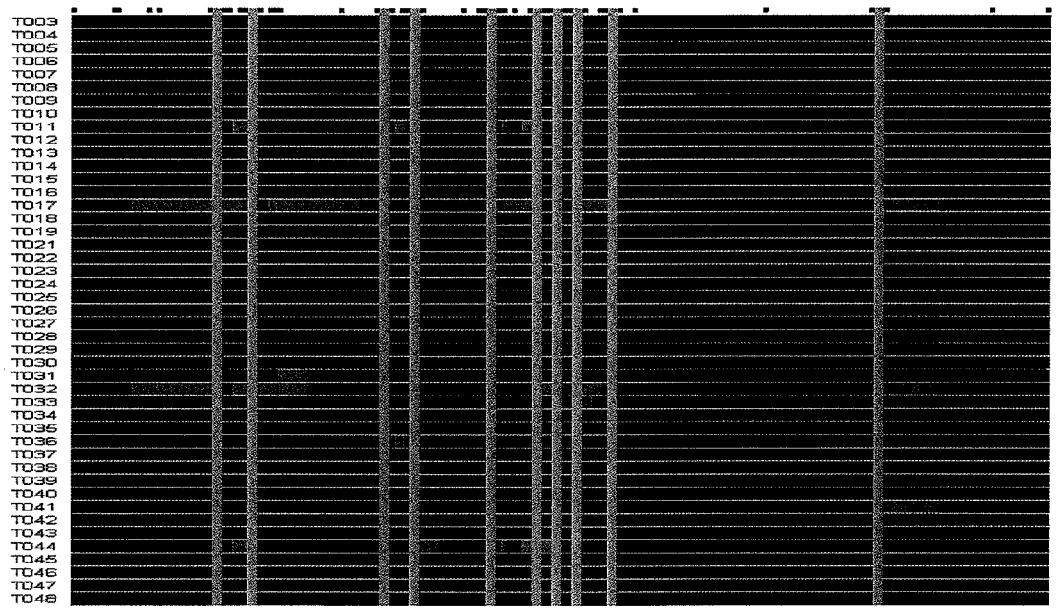
FIG. 10 shows the results of the AFLP analysis on SDR-0 and DH-0 plants. Every individual line represents a single DH-0 plant respectively a SDR-0 plant. Every column represents a linkage group.
Figure 10:
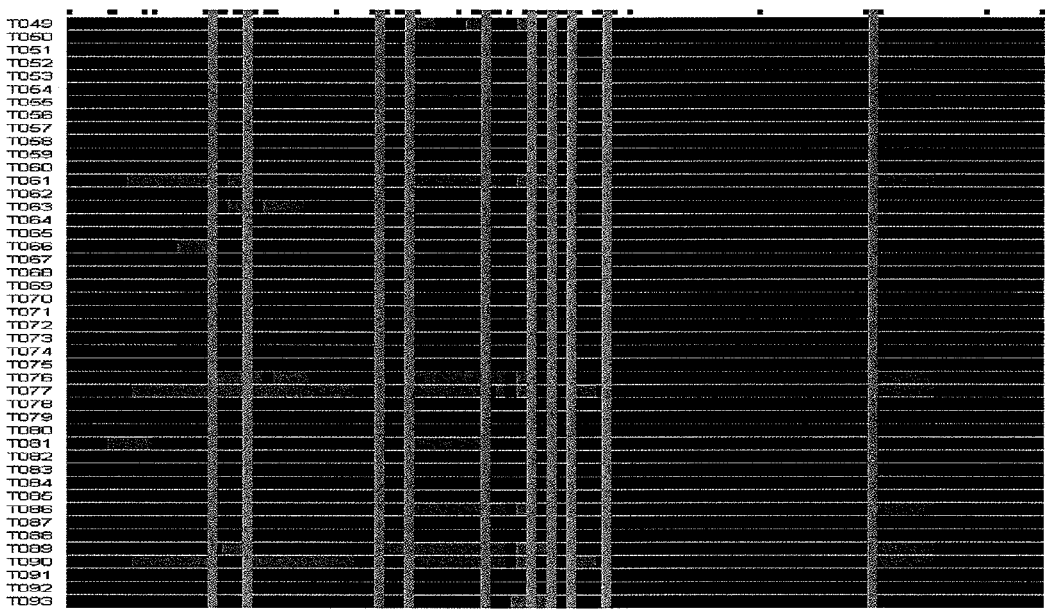

FIG. 10 shows the results of the AFLP analysis on SDR-0 and DH-0 plants. Every individual line represents a single DH-0 plant respectively a SDR-0 plant. Every column represents a linkage group. A clearly distinct classification can be made between DH lines and lines carrying a heterozygous segment (light grey areas). Segregation in the SDR-1 generation of the above mentioned traits is associated with the heterozygous segments accordingly.

6. Fine Mapping

Fine mapping of the locus that is responsible for the segregation in the SDR-1 generation is performed according to Peleman J et al., (2005) Genetics 171: 1341-1352.

Example 6

Enhancement of the Formation of Unreduced Spores/Gametes in Sweet Pepper (*Capsicum annuum* L.)

In order to increase the frequency of unreduced spore/gamete formation, cold stress was applied as an inducer, exactly as described by Zhang X et al. (2002, supra).

For this purpose, flowering plants of sweet pepper containing pre-meiotic floral buds and growing at 23° C. were exposed for 2 days to 11° C. After this cold shock, the buds were harvested and pollen were extracted by opening the anthers using dissecting forceps and scalpel. The pollen were subsequently transferred on a microscopic glass slide and stained for viability using a drop of aceto-carmine. Cover slides were put on top of the suspension which was investigated using light-microscopy.

Figure 9A:
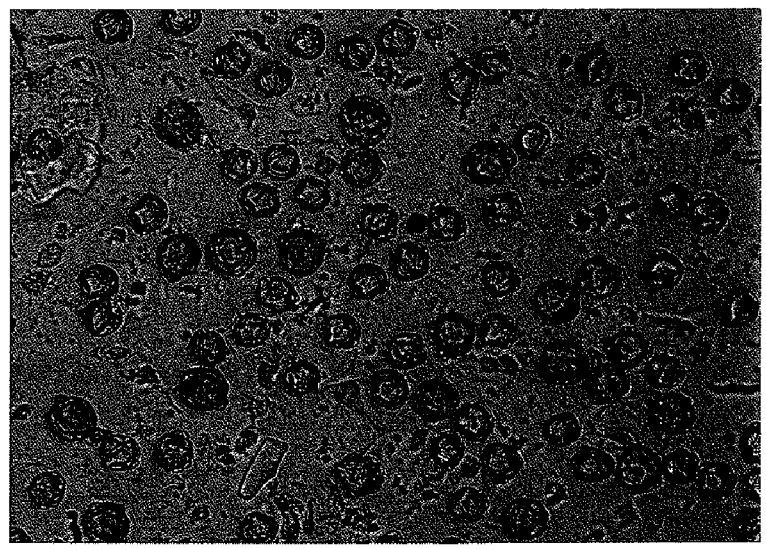
FIGS. 9A and 9B show representative examples of the morphologies of pollen collected from cold-treated plants (FIG. 9A) versus control plants (FIG. 9B).
Figure 9B:
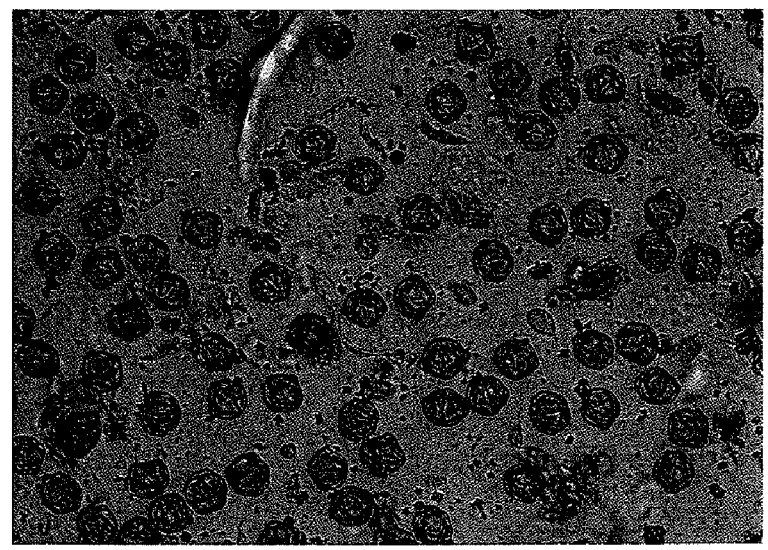

As a control, pollen was collected form sweet pepper plants which were grown at 23° C. FIG. 9 shows representative examples of the morphologies of the pollen collected from the cold-treated plants (FIG. 9A) versus the control plants (FIG. 9B). As can be seen, the number of pollen with a larger size indicative for being derived from unreduced spores is strongly increased for the cold-treated plant. In this particular example it was estimated that the % of enlarged spores mounted up to 25 due to the cold treatment. As such the enhancement of the formation of unreduced spores by temperature stress is shown to be highly feasible.

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

We claim:

1. A method for mapping traits in an organism comprising:
    a) providing a population of second division restitution (SDR)-0 organisms that each arise from one member of a population of unreduced SDR-0 cells resulting from second division restitution;
    b) producing a population of SDR-1 progeny organisms from each SDR-0 organism;
    c) phenotyping the SDR-1 progeny organisms within each of the SDR-1 progeny populations to identify segregating traits within each SDR-1 progeny population;
    d) for each SDR-1 progeny organism that exhibits segregating traits in a SDR-1 progeny population, genotyping the corresponding SDR-0 organism;
    e) genotyping the other SDR-0 organisms in the SDR-0 population which do not correspond to the SDR-1 progeny having the segregating traits,
    f) comparing the genotype of the SDR-0 organisms in (d) with the genotype of the other SDR-0 organisms in (e); and
    g) using the SDR-0 genotypes identified in (d)-(f) to identify in each SDR-0 organism heterozygous chromosomal regions associated with the segregating trait identified in the corresponding SDR-1 progeny population in (d).

2. The method as claimed in claim 1, wherein the population of unreduced SDR-0 cells that each give rise to an organism of the SDR-0 population is obtained by sorting a population of cells on the basis of size, mass, or DNA content and selecting the unreduced SDR-0 cells that have an increased size, mass, or DNA content as members of the population of unreduced SDR-0 cells.

3. The method as claimed in claim 2, wherein the unreduced SDR-0 cells are sorted by means of a flow cytometer, centrifuge, or manually with a micromanipulator.

4. The method as claimed in claim 1, wherein phenotyping the SDR-1 progeny organisms within the progeny populations is performed by means of visual observation or by analysis of content and/or composition of ions, transcripts, proteins, metabolites, or combinations thereof, in each SDR-1 organism.

5. The method as claimed in claim 4, wherein phenotyping is performed by means of phenomics, ionomics, transcriptomics, proteomics, metabolomics or combinations thereof.

6. The method as claimed in claim 1, wherein genotyping the SDR-0 organisms is performed by means of a method revealing nucleic acid polymorphisms.

7. The method as claimed in claim 6, wherein the method revealing nucleic acid polymorphisms is selected from amplified fragment length polymorphism (AFLP), restriction fragment length polymorphism (RFLP), single nucleotide polymorphism (SNP), single feature polymorphism (SFP), single sequence repeat (SSR), and rapid amplification of polymorphic DNA (RAPD).

8. The method as claimed in claim 1, wherein production of the organisms within the SDR-1 progeny populations is performed under varying conditions.

9. The method as claimed in claim 8, wherein the varying conditions are varying environmental conditions.

10. The method as claimed in claim 9, wherein the varying environmental conditions are selected from laboratory conditions and field conditions, wherein both types of conditions are varied with respect to weather conditions.

11. The method as claimed in claim 1, wherein the population of unreduced SDR-0 cells is produced by an organism selected to show an above-average second division restitution.

12. The method as claimed in claim 11, wherein the unreduced SDR-0 cells are produced by an organism genetically modified to show an above-average second division restitution.

13. The method as claimed in claim 12, wherein the genetic modification is transient.

14. The method as claimed in claim 12, wherein the genetic modification is by stable incorporation of a genetic element increasing the number of second division restitution events in the organism.

15. The method as claimed in claim 1, wherein the population of unreduced SDR-0 cells is produced by an organism that is subjected to environmental stress to show an above-average second division restitution.

16. The method as claimed in claim 15, wherein the environmental stress is selected from temperature stress, nitrogen dioxide, nitrous oxide, and combinations thereof.

17. The method as claimed in claim 1, wherein the SDR-0 organisms are plants and wherein the unreduced SDR-0 cells are spores.

* * * * *